US 6,453,198 B1

(12) United States Patent
Torgerson et al.

(10) Patent No.: US 6,453,198 B1
(45) Date of Patent: Sep. 17, 2002

(54) POWER MANAGEMENT FOR AN IMPLANTABLE MEDICAL DEVICE

(75) Inventors: Nathan A. Torgerson, Andover; James E. Riekels, New Hope, both of MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/560,755

(22) Filed: Apr. 28, 2000

(51) Int. Cl.[7] ............................................. A61N 1/18
(52) U.S. Cl. ........................................................... 607/29
(58) Field of Search ................................ 320/128, 130, 320/132; 324/426, 433; 600/374, 509; 607/2, 4, 5, 9, 11, 16, 27, 29, 34, 61, 116, 119, 120, 137, 33

(56) References Cited

U.S. PATENT DOCUMENTS

| | | | |
|---|---|---|---|
| 4,232,679 A | | 11/1980 | Schulman |
| 5,179,950 A | | 1/1993 | Stanislaw |
| 5,344,431 A | | 9/1994 | Merritt et al. |
| 5,354,320 A | | 10/1994 | Schaldach et al. |
| 5,733,313 A | | 3/1998 | Barreras, Sr. et al. |
| 5,735,887 A | | 4/1998 | Barreras, Sr. et al. |
| 5,752,977 A | | 5/1998 | Grevious et al. |
| 5,807,397 A | | 9/1998 | Barreras |
| 5,869,970 A | * | 2/1999 | Palm et al. .................. 324/433 |
| 5,876,425 A | | 3/1999 | Gord et al. |
| 5,941,906 A | | 8/1999 | Barreras, Sr. et al. |
| 5,991,664 A | | 11/1999 | Seligman |
| 5,991,665 A | | 11/1999 | Wang et al. |
| 6,154,675 A | * | 11/2000 | Juran et al. .................... 607/29 |

FOREIGN PATENT DOCUMENTS

| | | |
|---|---|---|
| JP | 640662 | 3/1994 |
| JP | 965635 | 3/1997 |
| WO | WO 99/06108 | 2/1999 |

OTHER PUBLICATIONS

Pump It Up.
Implantable Neurostimulation Systems Brochure, Medtronic, 1998.

* cited by examiner

Primary Examiner—Jeffrey P. Jastrzab
Assistant Examiner—Frances P. Oropeza
(74) Attorney, Agent, or Firm—Banner & Witcoff, Ltd.

(57) ABSTRACT

A power management system and technique to manage and allocate the energy provided to various components of an implanted device during periods of low energy. The power management system includes an implantable power source delivering energy to various components within the implantable medical device, a measurement device to measure the energy of the power source, and a processor responsive to the measurement device. The processor monitors the energy level of the power source. During periods of low energy, the processor limits the energy to certain device-critical components of the implantable medical device. This minimizes the risk of damage to the power source resulting from high energy drain during periods of low energy. Further, this preserves operation of device-critical components of the implanted device during periods of low energy.

37 Claims, 8 Drawing Sheets

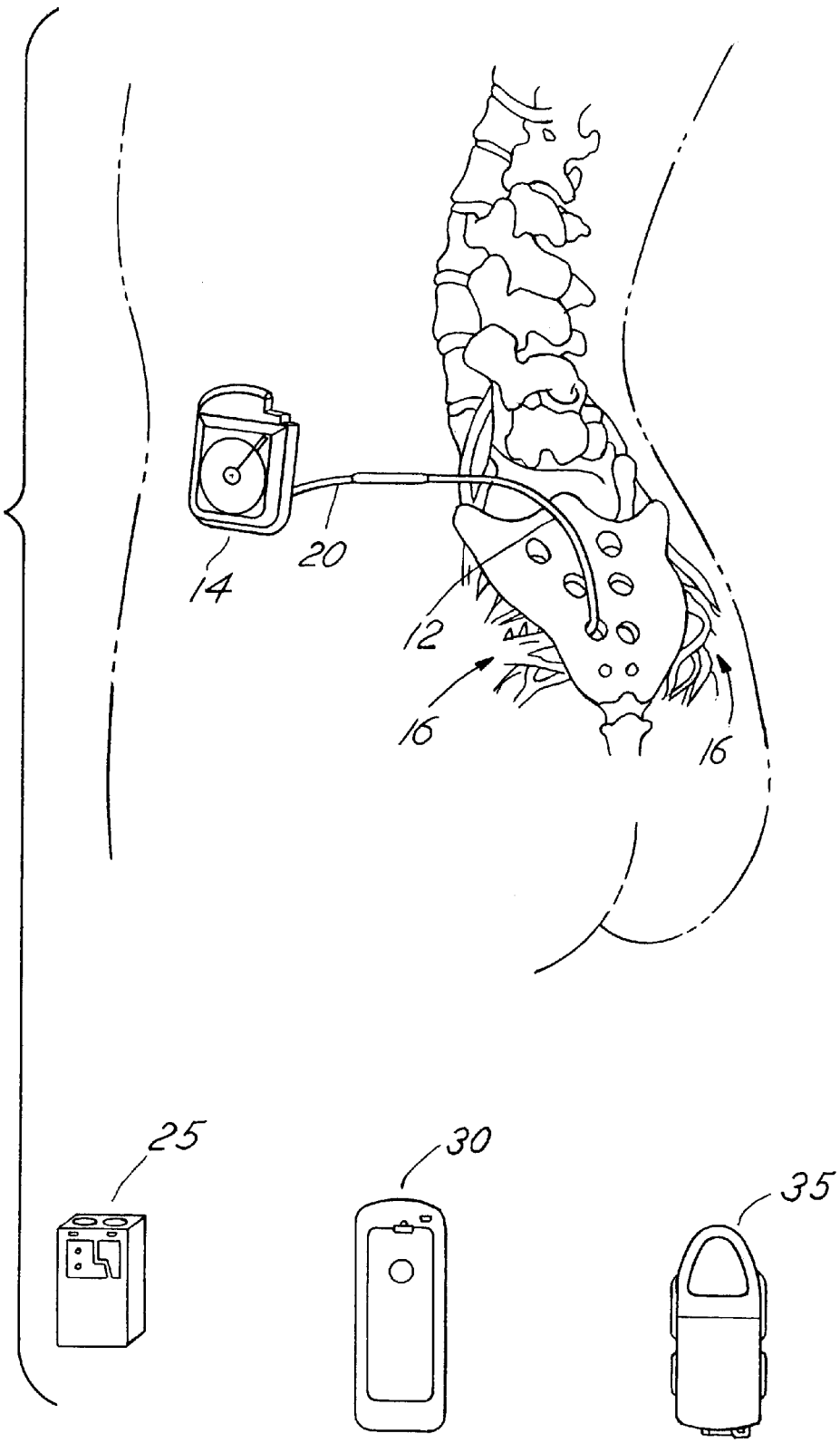

POWER MANAGEMENT FOR AN IMPLANTABLE MEDICAL DEVICE

BACKGROUND OF THE INVENTION

This patent application is related to the following patent applications filed herewith:

(1) U.S. patent application Ser. No. 09/561,566, entitled "Implantable Medical Pump with Multi-layer Back-up Memory," filed on Apr. 28, 2000, and having named inventors David C. Ullestad and Irfan Z. Ali;

(2) U.S. patent application Ser. No. 09/562,221, entitled "Battery Recharge Management for an Implantable Medical Device," filed on Apr. 28, 2000, and having named inventors Nathan A. Torgerson and James E. Riekels; and (3) U.S. patent application Ser. No. 09/561,479, entitled "Method and Apparatus for Programming an Implantable Medical Device," filed on Nov. 1, 2001.

FIELD OF INVENTION

This invention relates generally to implantable medical devices, and more particularly to power management techniques for implantable medical devices.

DESCRIPTION OF THE RELATED ART

The medical device industry produces a wide variety of electronic and mechanical devices for treating patient medical conditions. Depending upon the medical condition, medical devices can be surgically implanted or connected externally to the patient receiving treatment. Physicians use medical devices alone or in combination with drug therapies to treat patient medical conditions. For some medical conditions, medical devices provide the best, and sometimes the only, therapy to restore an individual to a more healthful condition and a fuller life.

Implantable medical devices are commonly used today to treat patients suffering from various ailments. Implantable medical devices can be used to treat any number of conditions such as pain, incontinence, movement disorders such as epilepsy and Parkinson's disease, and sleep apnea. Additional therapies appear promising to treat a variety of physiological, psychological, and emotional conditions. As the number of implantable medical device therapies has expanded, greater demands have been placed on the implantable medical device.

One type of implantable medical device is an Implantable Neuro Stimulator (INS). The INS delivers mild electrical impulses to neural tissue using an electrical lead. The neurostimulation targets desired neural tissue to treat the ailment of concern. For example, in the case of pain, electrical impulses (which are felt as tingling) may be directed to cover the specific sites where the patient is feeling pain. Neurostimulation can give patients effective pain relief and can reduce or eliminate the need for repeat surgeries and the need for pain medications.

Implantable medical devices such as neurostimulation systems may be partially implantable where a power source is worn outside the patient's body. This system requires an antenna to be placed on the patient's skin over the site of the receiver to provide energy and control to the implanted device. Typically, the medical device is totally implantable where the power source is part of the implanted device. The physician and patient may control the implanted system using an external programmer. Such totally implantable systems include, for example, the Itre® 3 brand neurostimulator sold by Medtronic, Inc. of Minneapolis, Minn.

In the case of an INS, for example, the system generally includes an implantable neurostimulator (INS) (also known as an implantable pulse generator (IPG)), external programmer(s), and electrical lead(s). The INS is typically implanted near the abdomen of the patient. The lead is a small medical wire with special insulation. It is implanted next to the spinal cord through a needle and contains a set of electrodes (small electrical contacts) through which electrical stimulation is delivered to the spinal cord. The lead is coupled to the INS via an implanted extension cable. The INS can be powered by an internal source such as a battery or by an external source such as a radio frequency transmitter. The INS contains electronics to send precise, electrical pulses to the spinal cord, brain, or neural tissue to provide the desired treatment therapy. The external programmer is a hand-held device that allows the physician or patient to optimize the stimulation therapy delivered by the INS. The external programmer communicates with the INS using radio waves.

Totally implantable medical devices, however, rely entirely on the implanted power source. Various INS components rely on the power source for energy, including for example, the signal generator for providing treatment therapy to the patient, the real time clock, the telemetry unit, and the memory. The signal generator is generally the primary energy drain for the power source. For those devices that have nonrechargeable batteries, the batteries last longer, however, the device must be surgically replaced when the power source is fully depleted. For those devices having rechargeable batteries, a surgical procedure is not required, however, the power source must be recharged more frequently since it cannot store as much energy.

In known systems, however, the continued operation of the signal generator during times of low energy unnecessarily drains the power source, thereby potentially depleting energy to device-critical INS components, such as the real time clock, the telemetry unit, and the memory. In the event that the power source runs low on energy, the implanted device can lose its treatment efficacy as well as its memory, its time, and its communications link with the external component. Further, when the power source is subsequently recharged, the INS may have to be reprogrammed and recalibrated according to the previous settings that were lost when the power source was fully depleted. The need for energy to handle the various functions of the implanted device is only going to increase.

Another disadvantage with known systems is that the power source can be damaged when it is being depleted at a high rate during periods when it has low voltage. This can occur, for example, when the implantable device is operating to provide treatment therapy with INS components having high-power requirements. For example, a 4.0 V battery that is below 2.75 V in stored energy is at risk of being damaged when it is being drained of 4 milliamps of current by the implanted device. Over time, with repeated draining of the battery at these critical setpoints would substantially reduce the efficacy of the battery and ultimately require surgical replacement of the implanted device.

Known implantable medical devices, for example, attempt to address the foregoing problems by providing low power or end-of-life warnings to the patient. For example, U.S. Pat. No. 5,344,431 discloses a method and apparatus for determination of battery end-of-service for implantable medical devices. This reference is incorporated herein by reference in its entirety. Such systems, however, continue to drain the battery until it is fully depleted without regard to preserving operation of the device-critical components.

Accordingly, there remains a need in that art to provide a power management system and technique for an implantable medical device that maintains operation of device-critical components during periods of low energy. Further, there remains a need in that art to provide a power management system and technique that allocates power source energy during periods of low energy.

SUMMARY OF THE INVENTION

The present invention provides a technique to manage and allocate the energy provided to various components of an implanted device during periods of low energy. In accordance with a preferred embodiment of the present invention, the power management system includes an implantable power source delivering energy to various components within the implantable medical device, a measurement device to measure the energy of the power source, and a processor responsive to the measurement device. The processor monitors the energy level of the power source. If the energy level falls below a first level, the processor shuts off energy to the therapy module of the implantable medical device while continuing to provide energy to the other device-critical components. If the energy level of the power source then falls below a second level, energy to even the device-critical components must be shut off. Eventually, the processor must prepare the entire implantable medical device to shut down. During recharge, when the energy level of the power source reaches a certain level, energy to all components is resumed.

Advantageously, this power management system and technique minimizes the risk of damage to the power source resulting from high energy drain during periods of low energy. Further, the present invention provides a technique to preserve operation of device-critical components of the implanted device during periods of low energy.

In alternative embodiments, the power management system of the present invention can be used with any number of implantable systems requiring a self-contained power source, including, but not limited to, pacemakers, defibrillators, and cochlear implants. In another alternative embodiment, the power management system of the present invention may be used with implantable diagnostic devices for detecting bodily conditions of certain organs, like the brain or the heart. In yet another alternative embodiment, the power management system of the present invention can be used within a drug delivery system having an implantable battery-powered pump. The power source in any of the these embodiments may be rechargeable or non-rechargeable. If rechargeable, the power source may be a lithium ion battery. The power source may also be a capacitive power source or any other source. The present invention serves to manage the energy of any of these power sources and to efficiently allocate the energy during times of low energy.

BRIEF DESCRIPTION OF THE DRAWINGS

FIG. 1 illustrates an implantable medical device in accordance with a preferred embodiment of the present invention, as implanted in a human body;

DESCRIPTION OF THE PREFERRED EMBODIMENTS

Figure 2A:
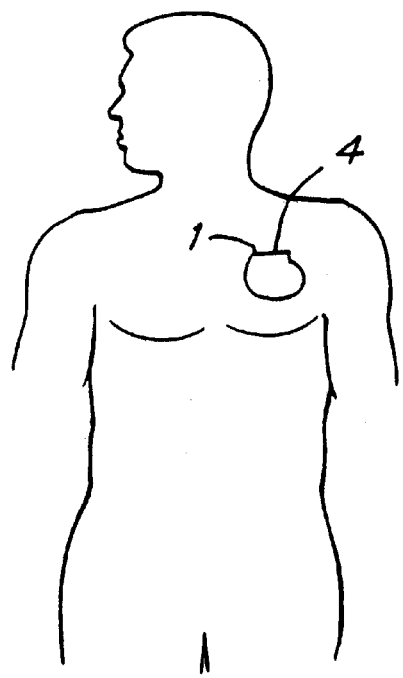
FIGS. 2A–D illustrates locations where the implantable medical device of the present invention can be implanted in the human body other than the location shown in FIG. 1.

The present invention is an power management system and method for an implantable medical device. The power management system provides an allocation of energy during periods when the implanted device has limited energy. In the preferred embodiment, the present invention is implemented within an implantable neurostimulator, however, those skilled in the art will appreciate that the present invention may be implemented generally within any implantable medical device having an implanted power source.

FIG. 1 shows the general environment of an Implantable Neuro Stimulator (INS) medical device 14 in accordance with a preferred embodiment of the present invention. The neurostimulation system generally includes an INS 14, a lead 12, a lead extension 20, an External Neuro Stimulator (ENS) 25, a physician programmer 30, and a patient programmer 35. The INS 14 preferably is a modified implantable pulse generator that will be available from Medtronic, Inc. with provisions for multiple pulses occurring either simultaneously or with one pulse shifted in time with respect to the other, and having independently varying amplitudes and pulse widths. The INS 14 contains a power source 315 and electronics to send precise, electrical pulses to the spinal cord, brain, or neural tissue to provide the desired treatment therapy. The power source 315 is discussed in further detail herein. As preferred, INS 14 provides electrical stimulation by way of pulses although other forms of stimulation may be used such as continuous electrical stimulation.

The lead 12 is a small medical wire with special insulation. The lead 12 includes one or more insulated electrical conductors with a connector on the proximal end and electrical contacts on the distal end. Some leads are designed to be inserted into a patient percutaneously, such as the Model 3487A Pisces-Quad® lead available from Medtronic, Inc. of Minneapolis Minn., and some leads are designed to be surgically implanted, such as the Model 3998 Specify® lead also available from Medtronic. The lead 12 may also be a paddle having a plurality of electrodes including, for example, a Medtronic paddle having model number 3587A. In yet another embodiment, the lead 12 may provide electrical stimulation as well as drug infusion. Those skilled in the art will appreciate that any variety of leads may be used to practice the present invention.

The lead 12 is implanted and positioned to stimulate a specific site in the spinal cord or the brain. Alternatively, the lead 12 may be positioned along a peripheral nerve or adjacent neural tissue ganglia like the sympathetic chain or it may be positioned to stimulate muscle tissue. The lead 12 contains one or more electrodes (small electrical contacts) through which electrical stimulation is delivered from the INS 14 to the targeted neural tissue. If the spinal cord is to be stimulated, the lead 12 may have electrodes that are epidural, intrathecal or placed into the spinal cord itself. Effective spinal cord stimulation may be achieved by any of these lead placements.

Although the lead connector can be connected directly to the INS 14, typically the lead connector is connected to a lead extension 20 which can be either temporary for use with an ENS 25 or permanent for use with an INS 14. An example of the lead extension 20 is Model 7495 available from Medtronic.

The ENS 25 functions similarly to the INS 14 but is not designed for implantation. The ENS 25 is used to test the efficacy of stimulation therapy for the patient before the INS 14 is surgically implanted. An example of an ENS 25 is a Model 3625 Screener available from Medtronic.

The physician programmer 30, also known as a console programmer, uses telemetry to communicate with the implanted INS 14, so a physician can program and manage a patient's therapy stored in the INS 14 and troubleshoot the patient's INS system. An example of a physician programmer 30 is a Model 7432 Console Programmer available from Medtronic. The patient programmer 35 also uses telemetry to communicate with the INS 14, so the patient can manage some aspects of her therapy as defined by the physician. An example of a patient programmer 35 is a Model 7434 Itrel® 3 EZ Patient Programmer available from Medtronic.

Those skilled in the art will appreciate that any number of external programmers, leads, lead extensions, and INSs may be used to practice the present invention.

Implantation of an Implantable Neuro Stimulator (INS) typically begins with implantation of at least one stimulation lead 12 usually while the patient is under a local anesthetic. The lead 12 can either be percutaneously or surgically implanted. Once the lead 12 has been implanted and positioned, the lead's distal end is typically anchored into position to minimize movement of the lead 12 after implantation. The lead's proximal end can be configured to connect to a lead extension 20. If a trial screening period is desired, the temporary lead extension 20 can be connected to a percutaneous extension with a proximal end that is external to the body and configured to connect to an External Neuro Stimulator (ENS) 25. During the screening period the ENS 25 is programmed with a therapy and the therapy is often modified to optimize the therapy for the patient. Once screening has been completed and efficacy has been established or if screening is not desired, the lead's proximal end or the lead extension proximal end is connected to the INS 14. The INS 14 is programmed with a therapy and then implanted in the body typically in a subcutaneous pocket at a site selected after considering physician and patient preferences. The INS 14 is implanted subcutaneously in a human body and is typically implanted near the abdomen of the patient.

Figure 2B:
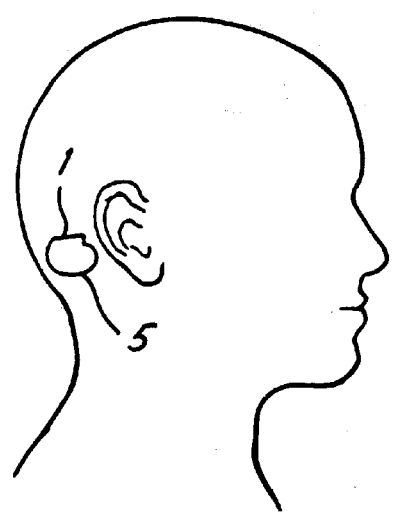
Figure 2C:
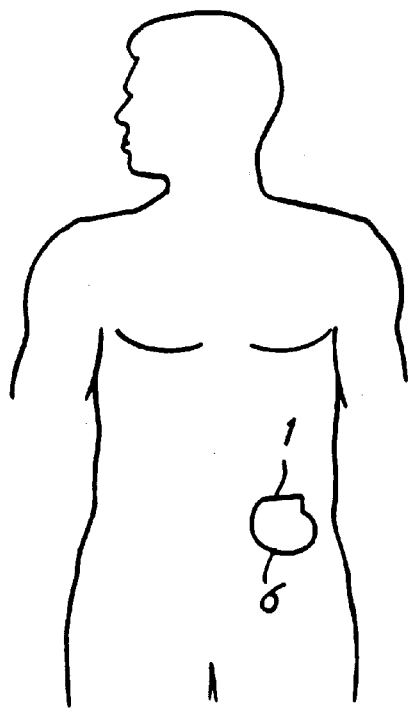
Figure 2D:
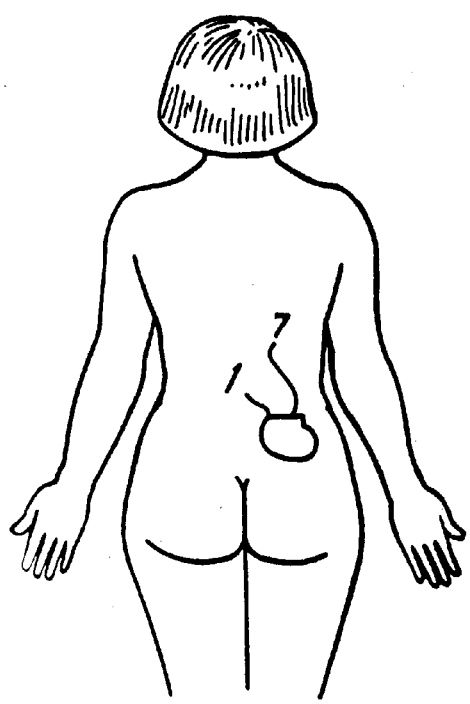

The above preferred embodiment for the placement of the INS 14 within the lower left abdominal region 6 of the patient is further illustrated in FIG. 2C. Other preferred embodiments for the placement of stimulator 1 within a human patient is further shown in FIGS. 2A, 2B, and 2D. As shown in FIG. 2A, the INS 14 can be implanted in a pectoral region 4 of the patient. As shown in FIG. 2B, the INS 14 can be implanted in a region 5 behind the ear of a patient, and more specifically in the mastoid region. As shown in FIG. 2D, the INS 14 can be placed in the lower back or upper buttock region 7 of the patient. The INS 14 is discussed in further detail herein.

The physician periodically uses the physician programmer 30 to communicate with the implanted INS 14 to manage the patient therapy and collect INS data. The patient uses the patient programmer 35 to communicate with the implanted INS 14 to make therapy adjustment that have been programmed by the physician, recharge the INS power source 315, and record diary entries about the effectiveness of the therapy. Both the physician programmer 30 and patient programmer 35 have an antenna or coil locator that indicates when the telemetry head is aligned closely enough with the implanted INS 14 for adequate telemetry.

Optionally, the neurostimulation system may include a sensor 25 to provide closed-loop feedback control of the INS 14. For example, the INS 14 may receive feedback instructions from an external component, which processes a recorded signal from the sensor 25 and sends instruction to signal generator via antenna or coil.

Figure 3:
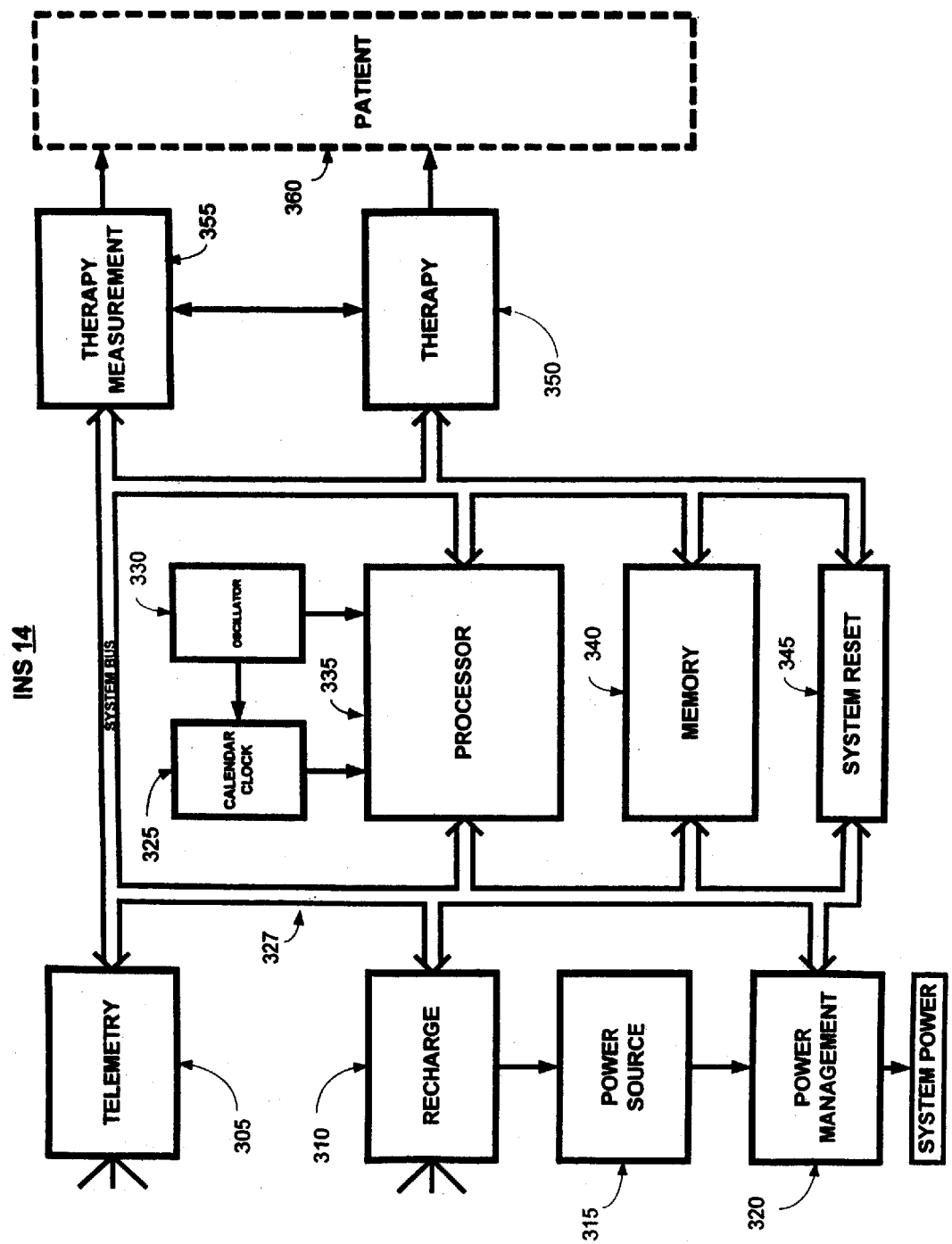
FIG. 3 is a schematic block diagram of an INS in accordance with a preferred embodiment of the present invention.

FIG. 3 is a schematic block diagram of an INS 14 in accordance with a preferred embodiment of the present invention. The implantable medical device generally includes a processor 335 with an oscillator 330, a calendar clock 325, memory 340, and system reset 345, a telemetry module 305, a recharge module 310, a power source 315, a power management module 320, a therapy module 350, and a therapy measurement module 335. Other components of the INS 14 can include, for example, a diagnostics module (not shown). All components except the power source 315 can be configured o n one or more Application Specific Integrated Circuits (ASICs), maybe part of one or more discrete components , or a combination of both . Also, all components except the oscillator 330, the calendar clock 325, and the power source 315 are connected to bi-directional data bus 327 that is non-multiplexed with separate address and data lines. The INS 14 generally includes a plurality of device-critical components including the calendar clock 325, the telemetry module 305, and the memory 340 (See Table B below). During periods of low energy, these components generally have a higher priority to the energy than other components such as, for example, the therapy module 350. These components are generally known in the art and are discussed in further detail herein.

The processor 335 is synchronous and operates on low energy such as a Motorola 68HC11 synthesized core operating with a compatible instruction set. The oscillator 330 operates at a frequency compatible with the processor 335, associated components, and energy constraints such as in the range from 100 KHz to 1.0 MHZ. The calendar clock 325 counts the number of seconds since a fixed date for date/time stamping of events and for therapy control such as circadian rhythm linked therapies. The memory 340 includes memory sufficient for operation of the INS 14 such as volatile Random Access Memory (RAM) for example Static RAM, nonvolatile Read Only Memory (ROM), Electrically Erasable Programmable Read Only Memory (EEPROM) for example Flash EEPROM, and register arrays configured on ASICs. Direct Memory Access (DMA) is available to selected modules such as the telemetry module 305, so the telemetry module 305 can request control of the data bus 327 and write data directly to memory 340 bypassing the processor 335. The system reset 345 controls operation of ASICs and modules during power-up of the INS 14, so ASICs and modules registers can be loaded and brought on-line in a stable condition.

Those skilled in the art will appreciate that the INS 14 may be configured in a variety of versions by removing modules not necessary for the particular configuration and by adding additional components or modules. All component of the INS 14 are contained within or carried on a housing that is hermetically sealed and manufactured from a biocompatible material such as titanium. Feedthroughs provide electrical connectivity through the housing while maintaining a hermetic seal, and the feedthroughs can be filtered to reduce incoming noise from sources such as cell phones.

Figure 4:
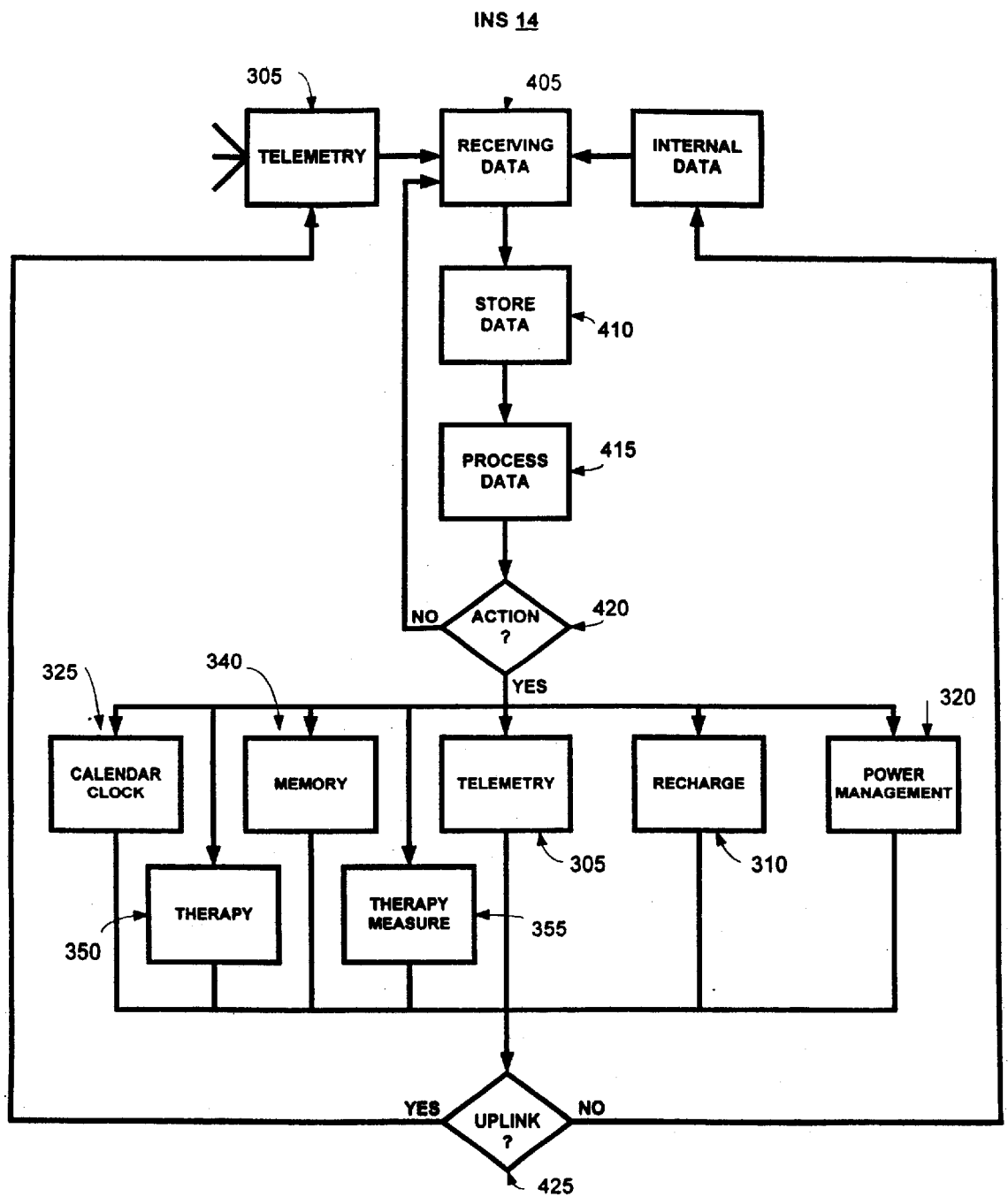
FIG. 4 depicts a general operation flowchart of the INS in accordance with a preferred embodiment of the present invention.

FIG. 4 depicts a general operation flowchart of the INS 14. At step 405, operation of the INS 14 begins with the processor 335 receiving data from either telemetry module 305 or from an internal source in the INS 14. At step 410, the received data is stored in a memory location. At step 415, the data is processed by the processor 335 to identify the type of data and can include further processing such as validating the integrity of the data. At step 420, after the data is processed, a decision is made whether to take an action. If no action is required, the INS 14 stands by to receive data. If an action is required, the action will involve one or more of the following modules or components: calendar clock 325, memory 340, telemetry 305, recharge module 310, power management 320, therapy module 350, and therapy measurement 355. An example of an action would be to recharge the power source 315. At step 425, after the action is taken, a decision is made whether the action is to be communicated or "uplinked" to a patient or physician programmer 35 or 30 through the telemetry module 305. If the action is uplinked, the action is recorded in the patient or physician programmer. If the action is not uplinked, the action is recorded internally within the INS 14.

Figure 5:
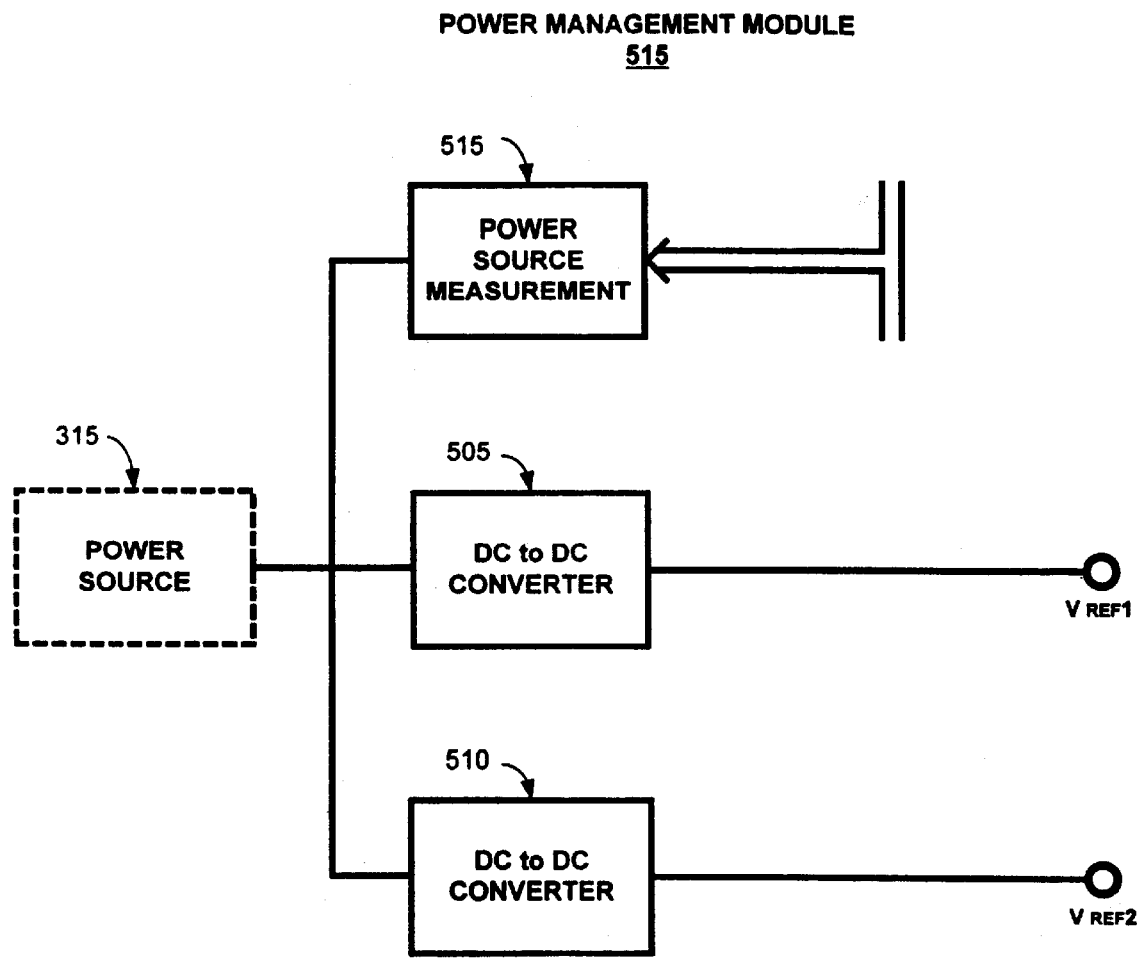
FIG. 5 is a schematic block diagram of the power management module in accordance with a preferred embodiment of the present invention.

FIG. 5 depicts a block diagram of the power management module 320 in accordance with a preferred embodiment of the present invention. The power management module 320 provides a stable DC power source to the INS 14 with voltages sufficient to operate the INS 14 such as between about 1.5 VDC and 2.0 VDC. The power management module 320 includes a first DC to DC converter 505, a second DC to DC converter 510, and power source measurement unit 515. One or more additional DC to DC converters can be added to the power management module 320 to provide additional voltage values for the INS 14. The first DC to DC converter 505 and second DC to DC converter 510 can be operational amplifiers configured for a gain necessary for the desired output voltage. The power source measurement unit 515 measures the power source 315 and reports this measurement to the processor 335, so the processor 335 can determine how to best allocate the power source 315, if necessary. In accordance with the present invention, if the processor 335 determines that the power source 315 is inadequate for normal operation, the processor 335 can instruct the power management module 320 to limit the energy to the device critical-components of the INS 14 or even to initiate a controlled shutdown of the INS 14. This process is discussed in further detail herein.

The INS power source 315 typically provides a voltage sufficient for the power management module 320 to supply energy to the INS 14 such as above 2.0 VDC, providing a maximum current in the range from about 5.0 mA to 30.0 mA for a time period adequate for the intended therapy. The INS power source 315 can be a physical storage source such as a capacitor or super capacitor, or the power source can be a chemical storage source such as a battery. The INS power source 315 can be a hermetically sealed rechargeable battery such as a lithium ion (Li+) battery or a non-rechargeable battery such as a lithium thionyl chloride battery. The ENS battery can be a non-hermetically sealed rechargeable battery such as nickel cadmium or a non-rechargeable battery such as an alkaline.

Figure 6:
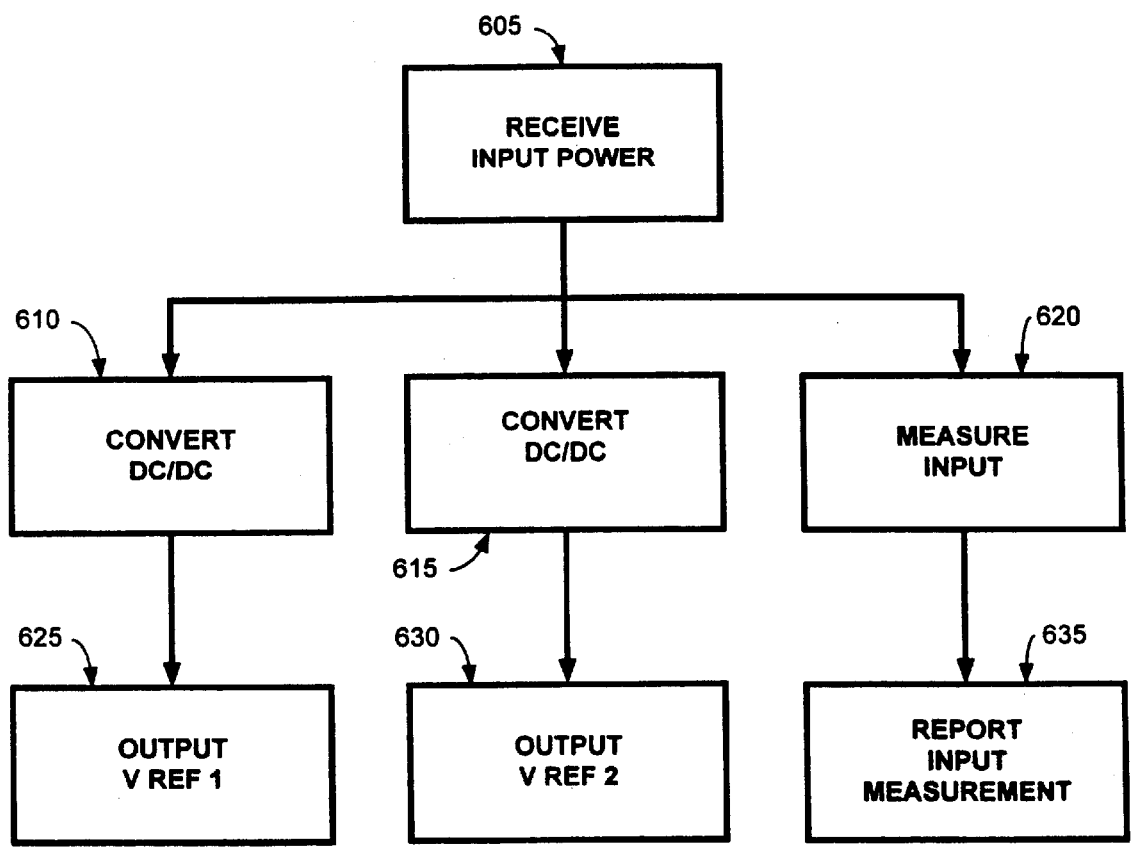
FIG. 6 is a flow chart depicting the operation of the power management module in accordance with a preferred embodiment of the present invention.

FIG. 6 is a flow chart depicting the operation of the power management module 320 in accordance with a preferred embodiment of the present invention. At step 605, the power management module 320 receives input energy from the power source. At steps 610 and 615, the energy is provided to DC to DC converters 505 and 510 before it is delivered, at steps 625 and 630, to various components within the INS 14. Also, at step 620, the power source measurement unit 515 measures the power source 315 and, at step 635, provides that information to the processor 335. The processor 335, in turn, determines how the energy from the power source 315 will be allocated, in accordance with procedures discussed herein, as a function of the battery voltage.

Figure 7:
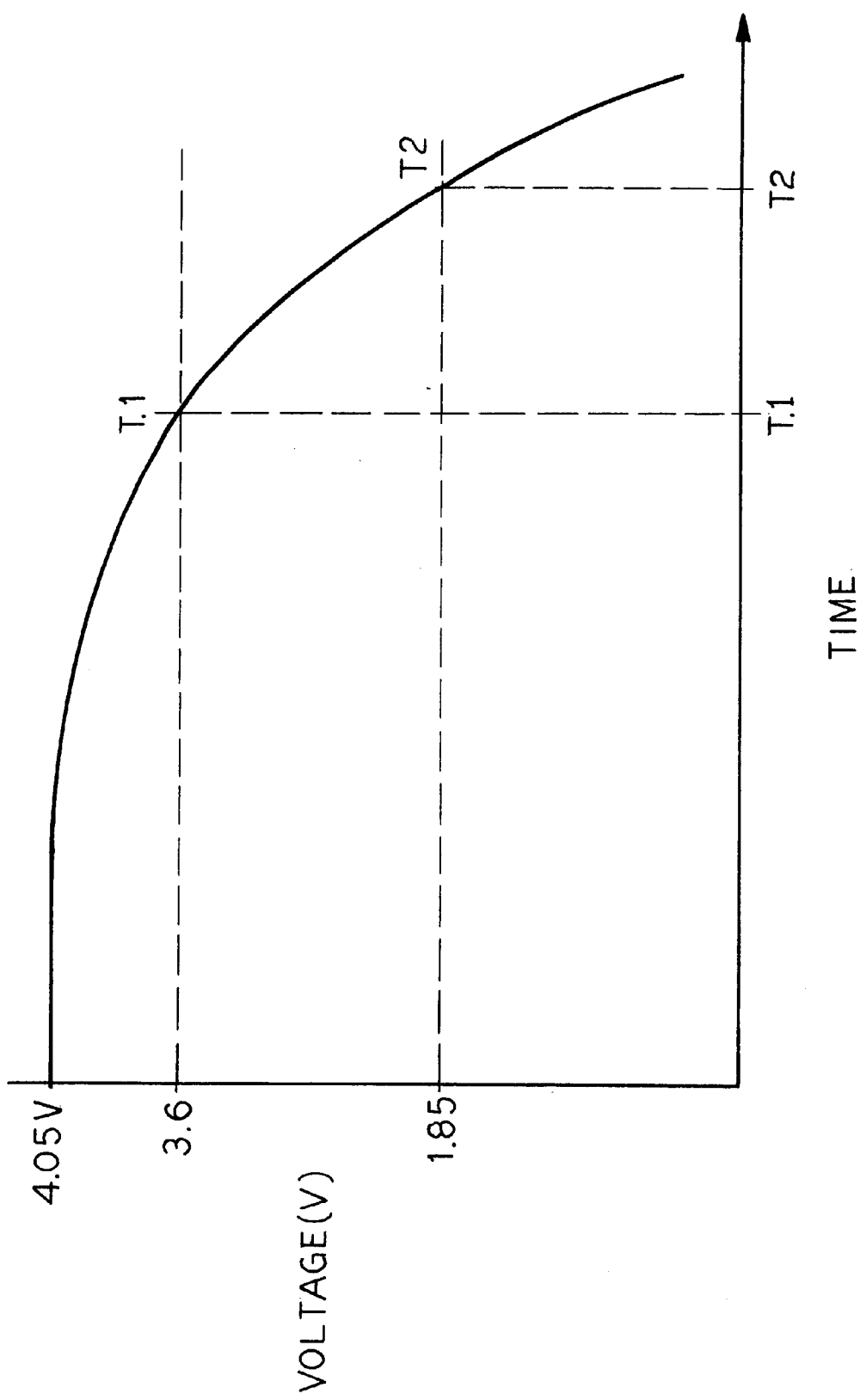
FIG. 7 is a chart depicting the change in power source energy over time for an implanted medical device in accordance with the present invention.

FIG. 7 is a chart depicting the change in power source energy over time for an implanted medical device in accordance with the present invention. The chart depicts the power source 315 being fully charged to being completely depleted. As shown in example of FIG. 7, at time t=0, the power source 315 is fully charged at 4.05 V (for a lithium ion power source). The voltage decreases over time, at first, gradually but rather precipitously after a certain point in time. The processor 335 periodically monitors the power source 315 and reacts accordingly as described herein. At a first transition point T1, the voltage is sufficiently low such that it becomes necessary to begin the process of limiting resources to the device-critical components of the INS 14. For a lithium ion battery as the power source 335, this first transition point T1 preferably is approximately 3.6 V and may be in the range of 3.85 V to 3.25 V. At a voltage of approximately 3.6 V, the INS 14 operates in a low power mode by restricting the energy provided to the INS components. In particular, energy is limited to the device-critical components such as the calendar clock 325, the telemetry unit 305, and the memory 340, while energy to the therapy module 350 and other components is suspended (See Table B below). In particular, energy is suspended to all unnecessary energy drains, such as unneeded level shifters. At the first transition point T1, the operation of the therapy module 350 to provide treatment therapy to the patient is suspended in efforts to preserve energy. Further, the INS 14 stores unsaved data in the memory 340 and the time/date of the calendar clock 325 into nonvolatile memory (such as an electrically erasable programmable read-only memory (EEPROM)) in the event that the power source 315 is drained completely. Data that may be stored in EEPROM may include, for example, new parameter data, measurement data, and patient information. Register values from therapy module 350 may also be stored in EEPROM. The processor 335 will also move into a sleep mode.

During this time period, since the treatment therapy has been suspended, it is anticipated that the patient will realize that the power source 315 is low and will recharge or replace the power source 315 to resume the treatment therapy. Alternatively, warning thresholds may be determined to give the patient warnings about depletion of the power source 315 as the power source 315 nears the first transition point T1. For example, warnings may be provided through the patient programmer 35 or an INS beeper.

During this period, if the INS 14 is interrogated by an external component, the INS 14 will provide a signal informing the external component that the power source 315 is near depletion or that it needs recharging.

If the power source 315 continues to drain in energy past a second transition point T2, the INS 14 must prepare to shut down. After this second transition point T2, only the recharge module 310 is operable. The recharge module 310 is necessary even at extremely low energy levels to control the recharging process of the power source 315 so as not to damage the power source 315. Further details of the recharge module 310 is disclosed in U.S. patent application Ser. No. 09/562,221, entitled "Battery Recharge Management Method and Apparatus for an Implantable Medical Device," having the same inventive entity and the same filing date as that of the present patent application. This co-pending patent application is incorporated herein by reference in its entirety.

As preferred, this second transition point T2 is approximately 1.85 V and may be in the range of 3.20 V to 1.85 V. At this point, the INS 14 preferably stores for a second time the memory 340 and the calendar clock 325 into nonvolatile memory. Advantageously, the storing of calendar clock 325 during the first and second transition points T1 and T2 provides information about the power source's discharge time.

The time period between the first and second transition points T1 and T2 may range one hour to one year, preferably between 3–6 months. During this time period, the power source 315 has an expected current drain of approximately 6 microamps. In contrast, during the time period before the first transition period, the expected current drain for the power source 315 is approximately 20 microamps to 4 milliamps. The current drain during this time period is much higher due the energy needed to operate the therapy module 350 such as a signal generator. The expected current drain after the second transition point T2 is approximately 1 microamp or less since almost every INS 14 component has been shut down. Advantageously, this low current drain prevents risk of damage to the power source 315.

The transition points T1 and T2 provide boundaries for the three states of operation: (1) normal operation state; (2) low power state; and (3) power off state. These transition points T1 and T2 may vary depending upon the type of power source. The following Table A provides the states of operation depending upon the power source:

TABLE A

| Power Source | Normal Operation | Low Power | Power Off |
|---|---|---|---|
| Primary Cell (CSVO, Hybrid) | 3.4 V–2.05 V | 2.00 V–1.85 V | 1.80 V and below |
| Alkaline | 3.0 V (1.5 × 2)–2.0 V | 2.00 V–1.85 V | 1.80 V and below |
| Lithium Ion | 4.05 V–3.85 (to 3.25 V) | 3.80 V–3.20 V (to 1.85 V) | 1.80 V and below |

Table B below lists the components of the INS 14 that active and inactive during each of the three states of operation:

TABLE B

| State of Operation | Components On | Components Off |
|---|---|---|
| Normal Operation | All | None |
| Low Power | Power Management 320<br>Recharge 310<br>Telemetry 305<br>Oscillator 330<br>Calendar Clock 325<br>Volatile Memory<br>High Freq Protection Circuit<br>High Energy Protection Circuit<br>System Shutdown/ POR 345 | Therapy 350<br>Measurement 355<br>Permanent Memory<br>Non-volatile Memory<br>EEPROM<br>Memory Management<br>System Bus 327<br>Processor 335 |
| Power Off | Recharge 310<br>High Freq. Protection Circuit<br>High Energy Protection Circuit | Therapy 350<br>Measurement 355<br>Permanent Memory<br>Non-volatile Memory<br>EEPROM<br>Memory Management<br>System Bus 327<br>Processor 335<br>Power Management 320<br>Telemetry 305<br>Oscillator 330<br>Calendar Clock 325<br>Volatile Memory<br>System Shutdown/POR 345 |

Figure 8:
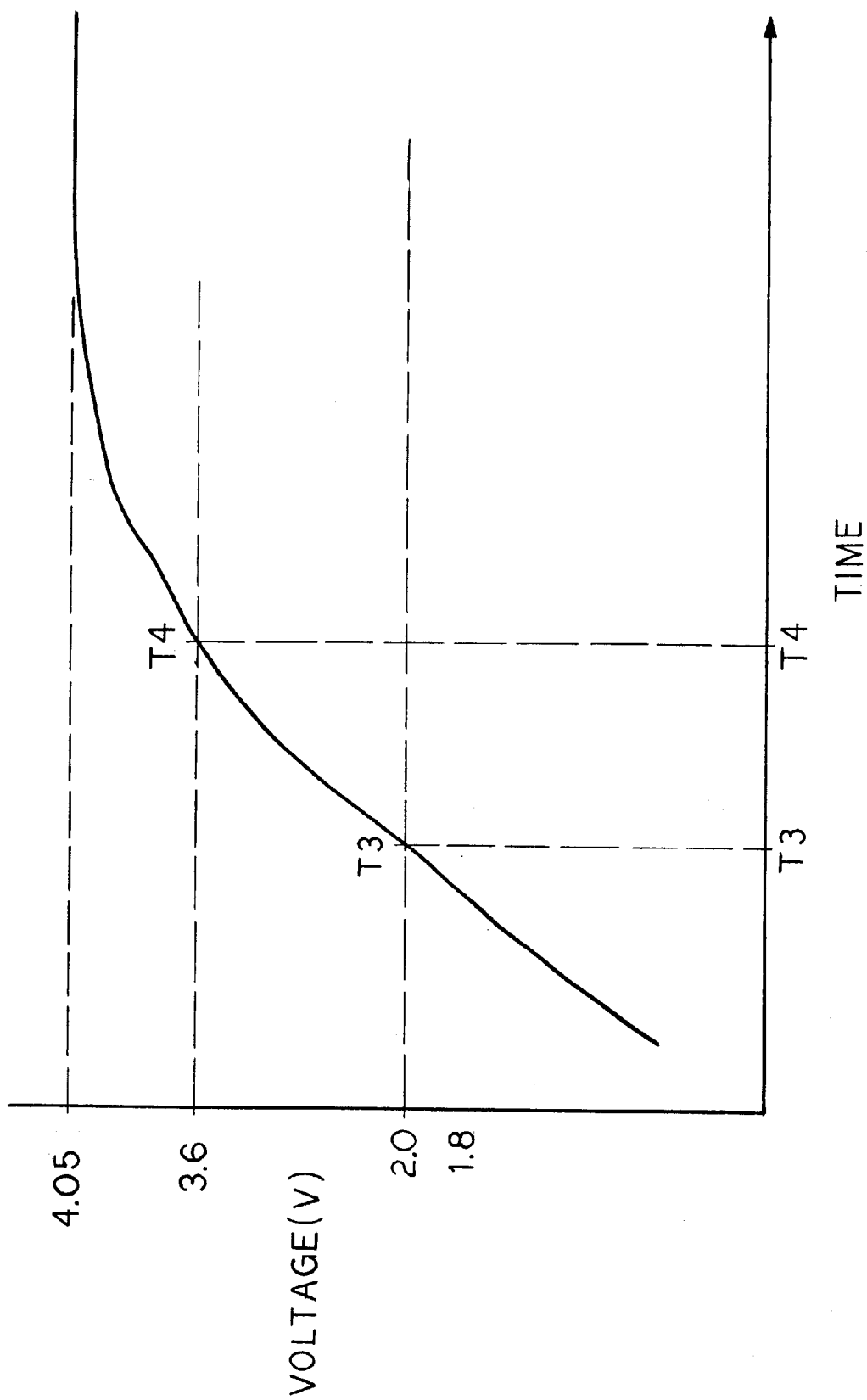
FIG. 8 is a chart depicting energy over time for an implanted medical device as the power source is being recharged from a depleted state.

During recharge, a different energy allocation scheme can be implemented during the recharging process. In this regard, FIG. 8 is a chart depicting energy over time for an implanted medical device as the power source 315 is being recharged from a depleted state. The recharging process is achieved by the magnetic recharge energy received from the external component 24. At a third transition point T3, the energy reaches approximately 2.0 V. Before this point, only the recharge module 310 is functional. After this point, each of the INS 14 components that were previously suspended are resumed. After the transition point T3, the processor 335 will load configuration data that was stored in the non-volatile memory such as the EEPROM. The processor 335 will also load a battery measurement from the power source measurement 515. The processor 335 during the recharge process will remain in sleep mode unless a telemetry communication is needed with the external charging device to provide closed-loop charging to maximize time and energy efficiencies.

At the fourth transition point T4, the power source level is 3.6 V. After this point, the processor 335 may begin operation of the INS 14 to provide treatment therapy. If a system reset is necessary, the treatment parameters stored in EEPROM will be loaded into RAM and the proper registers on the INS 14 to prepare to deliver therapy.

When the recharging process is stopped, the processor 335 will wake up to check the power source 315. If the energy is above 3.6 V, the INS 14 will function in normal operation. If the energy is below 3.6 V, the INS 14 will go into the low power state of operation (described above).

Initially, before the INS 14 is first implanted into the patient and charged for the first time, the power source 315 has an initial or a "shipping mode" setting. In shipping mode, the power source 315 is preferably near full charge but is at a low current drain due to the device-critical components. As preferred, the power source 315 is charged to approximately 3.8 V in shipping mode. Advantageously, the INS 14 may be shipped at normal voltage levels such that it may immediately provide treatment therapy upon implant without requiring a charging process. Further, this allows the physician to immediately test the implanted device during the surgical procedure.

Those skilled in the art will appreciate that other power-up and power-down techniques may be implemented. For example, the transition points may be dynamic points that are based on a number of factors including, for example, the rate of change of the energy of the power source 315, namely the slope of the curves of FIGS. 7 and 8. Advantageously, this factor ensures that the current drain is not damaging the battery. Another factor that may be considered is the age of the battery. With an older the battery, the transition points may need to be varied. Another factor is the energy demands of the therapy. If the therapy has limited energy demands, then the first transition point may be occur at a later point in time. Further, additional transition points may be included. For example, there may be a point before T1 (FIG. 7) where a warning signal may be provided to the patient before the treatment therapy is turned off.

In alternative embodiments, the power management system of the present invention can be used with any number of implantable systems requiring a self-contained power source, including, but not limited to, pacemakers, defibrillators, and cochlear implants. In another alternative embodiment, the power management system of the present invention may be used with implantable diagnostic devices for detecting bodily conditions of certain organs, like the brain or the heart. In yet another alternative embodiment, the power management system of the present invention can be used within a drug delivery system having an implantable battery-powered pump. The power source in any of the these embodiments may be rechargeable or non-rechargeable. If rechargeable, the power source may be a lithium ion battery. The power source may also be a capacitive power source or any other source. The present invention serves to manage the energy of any of these power sources and to efficiently allocate the energy during times of low energy.

Those skilled in that art will recognize that the preferred embodiments may be altered or amended without departing from the true spirit and scope of the invention, as defined in the accompanying claims. Thus, while various alterations and permutations of the invention are possible, the invention is to be limited only by the following claims and equivalents.

We claim:

1. A power management system for an implantable medical device comprising in combination:
   (a) an implantable power source delivering energy to at least two components within the implantable medical device;
   (b) a measurement device to measure the energy of the power source; and
   (c) a processor responsive to the measurement device and capable of limiting energy to only a recharge module if the energy of the power source falls below a predetermined critical level.

2. The power management system of claim 1, wherein the power source is selected from the group consisting of a rechargeable battery, a nonrechargeable battery, and a capacitive power source.

3. The power management system of claim 1, wherein the power source is a lithium ion power source.

4. The power management system of claim 1, wherein the implantable medical device is an implantable signal generator.

5. The power management system of claim 1, wherein the implantable medical device is an implantable drug pump.

6. The power management system of claim 1, wherein the implantable medical device is selected from the group consisting of a pacemaker, a defibrillator, a cochlear implant, and an implantable diagnostic device.

7. The power management system of claim 1, wherein (b) and (c) are part of at least one integrated circuit.

8. The power management system of claim 1, wherein (b) and (c) are part of at least one discrete component.

9. The power management system of claim 1, wherein (a)–(c) are contained within a single hermetically-sealed housing.

10. The power management system of claim 1, wherein the processor is further responsive to the measurement device, wherein if the energy of the power source falls below a first predetermined level, the processor is capable of limiting energy to at least one component while allowing energy to at least one other component.

11. The power management system of claim 10, wherein the other component is a device-critical component selected from the group consisting of a clock, a memory, a recharge module, and a telemetry module.

12. The power management system of claim 10, wherein the one component is a therapy module.

13. The power management system of claim 10, further comprising at least one converter delivering energy from the power source to the at least one component.

14. The power management system of claim 10, wherein the first predetermined level is based on voltage of the power source.

15. The power management system of claim 10, wherein the first predetermined level is based on at least one factor selected from the group consisting of voltage of the power source, age of the power source, and energy demand for a treatment therapy.

16. A power management system for an implantable medical device comprising in combination:
   (a) an implantable power source delivering energy to at least two components within the implantable medical device;
   (b) a measurement device to measure the energy of the power source; and
   (c) a processor responsive to the measurement device and capable of limiting energy to a recharge module if the energy of the power source falls below a predetermined level, the processor further capable of shutting down the implantable medical device if the energy of the power source falls below a second predetermined level.

17. A power management system for an implantable medical device comprising in combination:
   (a) an implantable power source delivering energy to at least one component within the implantable medical device;
   (b) a measurement device to measure the energy of the power source; and
   (c) a processor responsive to the measurement device and capable of limiting energy to a recharge module if the energy of the power source falls below a predetermined critical level.

18. A power management system for an implantable medical device comprising in combination:
   (a) an implantable power source delivering energy to at least one device-critical component and at least one therapy component within the implantable medical device;
   (b) a measurement device to measure the energy of the power source; and
   (c) a processor responsive to the measurement device and capable of limiting energy to a recharge module if the energy of the power source falls below a predetermined critical level.

19. A method of managing a power source within an implantable medical device comprising the steps of:

(a) measuring an energy level of the power source;

(b) limiting energy to a therapy component if the energy level of the power source falls below a first predetermined level, while still providing energy to at least one device-critical component; and (c) limiting energy to all other components except a recharge component if the power level falls below a second predetermined level.

20. The method of managing a power source of claim 19, wherein the step of restricting energy to all other components further includes the step of preparing the implantable medical device to shut down.

21. The method of managing a power source of claim 19, wherein the step of limiting energy to a therapy component further includes the step of storing in memory a time when the energy level falls below the first predetermined level.

22. The method of managing a power source of claim 19, wherein the step of restricting energy to all other components further includes the step of storing in memory a time when the energy level falls below the second predetermined level.

23. The method of managing a power source of claim 19, further comprising the step of:

(d) warning a patient of low energy if the energy level falls below a second predetermined level.

24. An implantable medical device comprising in combination:

(a) a lead which is adapted to provide treatment to a predetermined site within a body of a patient;

(b) an implantable power source delivering energy to at least two components within the implantable medical device; and (c) a measurement device to measure the energy of the power source; and (d) a processor responsive to the measurement device and capable of limiting energy to only a recharge module if the energy of the power source falls below a predetermined critical level.

25. The implantable medical device of claim 24, wherein the power source is selected from the group consisting of a rechargeable battery, a nonrechargeable battery, and a capacitive power source.

26. The implantable medical device of claim 24, wherein the power source is a lithium ion power source.

27. The implantable medical device of claim 24, wherein the implantable medical device is an implantable signal generator.

28. The implantable medical device of claim 24, wherein the implantable medical device is an implantable drug pump.

29. The implantable medical device of claim 24, wherein the implantable medical device is selected from the group consisting of a pacemaker, a defibrillator, a cochlear implant, and an implantable diagnostic device.

30. The implantable medical device of claim 24, wherein the processor is further responsive to the measurement device, wherein if the energy of the power source falls below a first predetermined level, the processor is capable of limiting energy to at least one component while allowing energy to at least one other component.

31. The implantable medical device of claim 30, wherein the other component is a device-critical component selected from the group consisting of a clock, a memory, a recharge module, and a telemetry module.

32. The implantable medical device of claim 30, wherein the one component is a therapy module.

33. The implantable medical device of claim 30, further comprising at least one converter delivering energy from the power source to the at least one component.

34. The implantable medical device of claim 30, wherein the processor is further capable of shutting down the implantable medical device if the energy of the power source falls below the predetermined critical level.

35. The implantable medical device of claim 30, wherein the first predetermined level is based on voltage of the power source.

36. The implantable medical device of claim 30, wherein the first predetermined level is based on at least one factor selected from the group consisting of voltage of the power source, age of the power source, and energy demand for a treatment therapy.

37. A power management system for an implantable medical device comprising in combination:

(a) an implantable power source delivering energy to at least two components within the implantable medical device;

(b) a measurement device to measure the energy of the power source; and (c) means for limiting energy to only a recharge module if the energy of the power source falls below a predetermined critical level.

\* \* \* \* \*